United States Patent [19]

Maulding et al.

[11] Patent Number: 4,459,408
[45] Date of Patent: Jul. 10, 1984

[54] PROCESS FOR THE PREPARATION OF 2-(5-ISOPROPYL-5-METHYL-4-OXO-2-IMIDAZOLIN-2-YL)-3-QUINOLINE-CARBOXYLIC ACID AND ALKYL 2-TRICHLOROMETHYL-3-QUINOLINE-CARBOXYLATE INTERMEDIATES THEREFOR

[75] Inventors: Donald R. Maulding, Somerville; Robert F. Doehner, Jr., East Windsor, both of N.J.

[73] Assignee: American Cyanamid Company, Stamford, Conn.

[21] Appl. No.: 381,813

[22] Filed: May 25, 1982

[51] Int. Cl.$^3$ .................. C07D 401/02; C07D 215/54
[52] U.S. Cl. ..................................... 546/167; 548/337; 546/170
[58] Field of Search ................................ 546/167, 170

[56] References Cited
PUBLICATIONS

Borsche et al., Berichte der Deutchen Chemischen Gesellschaft, 76, pp. 1099–1104, (1943).
Staiks J.A.C.S., 93, (1971), pp. 195–199.
Rodd, (vol. IV, pt. A), Chem. of Carbon Cmpds., (1957), p. 305, E. Sevier, N.Y., N.Y.

Primary Examiner—Paul M. Coughlan, Jr.
Assistant Examiner—D. B. Springer
Attorney, Agent, or Firm—H. G. Jackson

[57] ABSTRACT

The invention is related to a novel process for the prepartion of 2-(5-isopropyl-5-methyl-4-oxo-2-imidazolin-2-yl)-3-quinolinecarboxylic acid, a useful and valuable herbicide.

4 Claims, No Drawings

PROCESS FOR THE PREPARATION OF 2-(5-ISOPROPYL-5-METHYL-4-OXO-2-IMIDAZOLIN-2-YL)-3-QUINOLINE-CARBOXYLIC ACID AND ALKYL 2-TRICHLOROMETHYL-3-QUINOLINE-CARBOXYLATE INTERMEDIATES THEREFOR

SUMMARY OF THE INVENTION

The invention is a process for the preparation of the herbicidal compound: 2-(5-isopropyl-5-methyl-4-oxo-2-imidazolin-2-yl)-3-quinolinecarboxylic acid of formula (I)

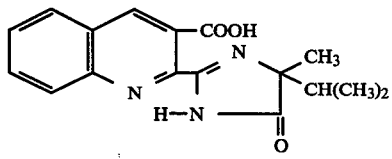

This compound is described in the application for U.S. Patent of Marcinus Los, Ser. No. 382,041, filed concurrently herewith and incorporated herein by reference thereto.

Thus, the compound of formula (I) may be prepared by reacting one molar equivalent of 2,3-quinolinedicarboxylic anhydride (II) with at least one molar equivalent of 2-amino-2,3-dimethylbutyramide (III) in the presence of an inert solvent and the resulting mixture of 2,3-quinolinedicarboxylic acid monoamides (IVa and IVb) is cyclized using base catalysis. This reaction scheme may be illustrated as follows:

We now find, that by the novel process of the invention the desired herbicide of formula (I) may be prepared by a convenient route as hereinbelow discussed and graphically illustrated in detail.

Thus, a lower alkyl ester of 2-methyl-3-quinolinecarboxylic acid (V) is reacted in the presence of an inert, anhydrous solvent, such as acetic acid or propionic acid and an acid acceptor such as sodium or potassium acetate at elevated temperatures of from about 100° C. to about 120° C. with chlorine gas for a period of time sufficient to essentially complete the reaction and obtain the desired lower alkyl ester of 2-trichloromethyl-3-quinolinecarboxylic acid (VI). This compound (VI) may be isolated from the reaction mixture by standard laboratory procedures as by precipitation or evaporation of the reaction solvent and the like. The thus isolated crude product (VI) may be further purified, if so desired, by standard laboratory procedures, such as recrystallization, column chromatography and the like.

Next, one molar equivalent of the formula (VI) 2-trichloromethyl compound is reacted with from about one molar equivalent to about 2 molar equivalent of 2-amino-2,3-dimethylbutyramide in the presence of an inert solvent such as benzene, toluene or xylene, and in the presence of from about 3 molar equivalents to about 5 molar equivalents of anhydrous sodium or potassium hydroxide, 2 molar equivalents of anhydrous sodium or potassium carbonate and from about 0.1 molar equivalent to about 0.3 molar equivalents of a phase transfer catalyst such as tetra($C_3$-$C_6$)alkylammonium salts, benzyl tri($C_1$-$C_6$)alkylammonium salts, crown others, tetraalkylphosphonium salts and the like at a temperature range of from about 80° C. to about 134° C. or at about the atmospheric boiling point of the solvent selected,

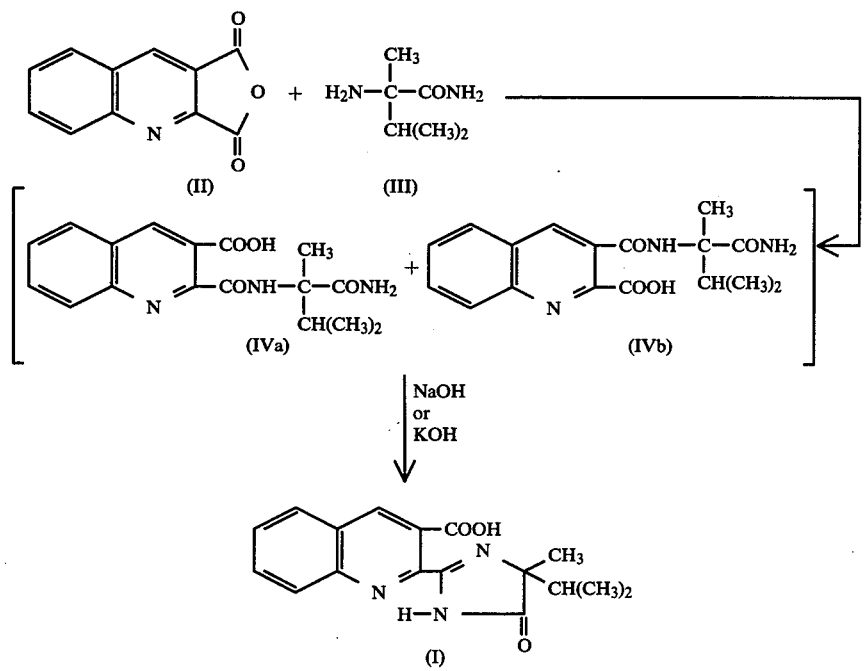

The above described and illustrated base-catalyzed cyclization of the formula (IVa) and (IVb) amides is described in the application for United States Patent of Jerry Michael Barton, Don Wesley Long and Kenneth Dale Lotts, Ser. No. 381,818, filed concurrently herewith and incorporated herein by reference thereto.

for a period of time sufficient to essentially complete the reaction. The thus obtained compound of formula (I) may be isolated from the reaction mixture by standard laboratory procedures. The above reaction scheme may be illustrated as follows:

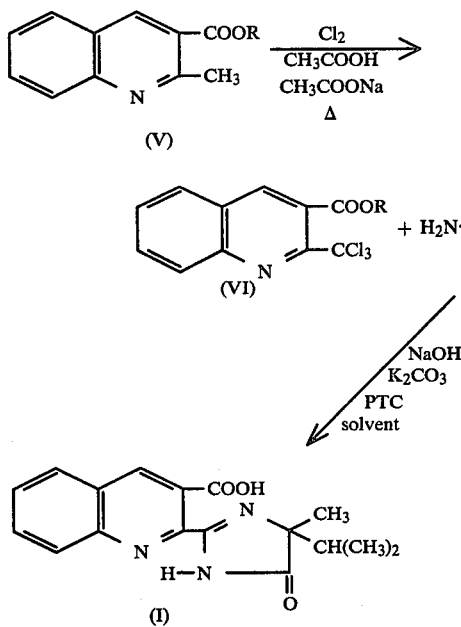

wherein R is $C_1$–$C_3$ alkyl; PTC stands for phase transfer catalyst.

As stated above, the compound of formula (I) is a useful herbicide. Since salts of this compound are water soluble, the compound can simply be dispersed in water and applied as a dilute aqueous spray to the foliage of plants or to soil containing propagating organs thereof.

The compound can also be formulated as wettable powders, flowable liquid, emulsifiable concentrates, granular formulations and the like.

Wettable powders can be prepared by grinding together about 20% to 45% by weight of a finely divided carrier such a kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims.

EXAMPLE 1

Preparation of 2-(5-isopropyl-5-methyl-4-oxo-2-imidazolin-2-yl)-3-quinolinecarboxylic acid A mixture of 3.84 g (0.012 mol) of ethyl 2-trichloromethyl-3-quinolinecarboxylate, 1.56 g (0.012 mol) of racemic 2-amino-2,3-dimethylbutyramide, 1.60 g (0.04 mol) of powdered sodium hydroxide, 3.28 g (0.024 mol) of anhydrous potassium carbonate, 0.40 g (0.0012 mol) of tetrabutylammonium hydrogen sulfate and 60 ml of toluene is heated at reflux for two hours under a blanket of nitrogen, while some toluene insoluble liquid is being separated out and removed from the reaction mixture. Next, the mixture is cooled to room temperature, 30 ml of water is added and the whole stirred until the precipitated solid is dissolved. The aqueous layer is separated and added to a solution of 10 ml concentrated hydrochloric acid in 40 ml of water to precipitate a red-brown solid, wt: 1.39 g. HPLC analysis indicates that 22% of this solid, or 0.31 g is the title compound.

Extraction of the aqueous filtrate with methylene chloride (3×30 ml) yields 0.48 g of a light yellow solid, analysis of which indicates that 86% or 0.41 g is the title compound.

Thus, 0.71 g of product is obtained (yield: 19%).

EXAMPLE 2

Preparation of ethyl 2-trichloromethyl-3-quinolinecarboxylate

A solution of 10.0 g (0.0465 mol) of ethyl 2-methyl-3-quinolinecarboxylate and 15.2 g (0.186 mol) of anhydrous sodium acetate in 100 ml of acetic acid is stirred and heated at 110°–115° C. Chlorine gas is bubbled through the above solution, at a slow rate, for three hours, while the temperature of the reaction mixture is maintained at 110°–115° C. The reaction mixture was then cooled down, and the excess chlorine gas removed by aeration of the mixture. The mixture is then diluted with methylene chloride, filtered and concentrated to about 75 ml volume. Next, saturated sodium carbonate solution is added in small portions until the acetic acid present is neutralized. The organic layer is separated, concentrated with heating, diluted with hexane, and reconcentrated to a volume of about 100 ml. The precipitate formed is filtered, triturated with hexane and dried to yield 14.0 g of a yellow solid. Recrystallized from an ehter-petroleum ether solution, the solid has a mp of 66° to 75° C.

EXAMPLE 3

Postemergence herbicidal evaluation of test compounds

The postemergence herbicidal activity of the compound of the present invention is demonstrated by the following tests, wherein a variety of monocotyledonous and dicotyledonous plants are treated with the compound dispersed in aqueous acetone mixtures. In the tests, seedling plants are grown in jiffy flats for about two weeks. The test compound is dispersed in 50/50 acetone/water mixtures containing 0.5% TWEEN ®20, a polyoxyethylene sorbitan monolaurate surfactant of Atlas Chemical Industries, in sufficient quantity to provide the equivalent of about 0.016 to 10 kg per hectare of active compound when applied to the plants through a spray nozzle operating at 2.8 kg cm$^{-2}$ pressure for a predetermined time. After spraying, the plants are placed on greenhouse benches and are cared for in the usual manner, commensurate with conventional greenhouse practices. From 4 to 5 weeks after treatment, the seedling plants, are examined and rated according to the rating system provided below. The data obtained are recorded in Table I below.

| Plant Species Used | |
| --- | --- |
| Green foxtail | (*Setaria viridis*) |
| Purple nutsedge | (*Cyperus rotundus* L.) |
| Wild oats | (*Avena fatua*) |
| Quackgrass | (*Agropyron repens*) |
| Field bindweed | (*Convolvulus arvensis* L.) |
| Cocklebur | (*Xanthium pensylvanicum*) |
| Morningglory | (*Ipomoea purpurea*) |
| Ragweed | (*Ambrosia artemisiifolia*) |
| Velvetleaf | (*Abutilon theophrasti*) |
| Barley | (*Hordeum vulgaret*) |
| Corn | (*Zea mays*) |
| Rice | (*Oryza sativa*) |
| Soybean | (*Glycine max*) |
| Sunflower | (*Helianthus annus*) |
| Wheat | (*Triticum aestivum*) |

TABLE I

POST-EMERGENCE TESTS - RATES IN KG/HA

| Compound | RATE | BARN-YARD-GR | GREEN FOX | P NUT SEDGE | WILD OATS | QUACK GRASS | FLD B INDWD | MRNGL RY SP |
| --- | --- | --- | --- | --- | --- | --- | --- | --- |
| 2-(5-Isopropyl-5- | 1.000 | 9.0 | 9.0 | 9.0 | 9.0 | 9.0 | 8.5 | 9.0 |
| methyl-4-oxo-2- | .500 | 8.7 | 9.0 | 8.3 | 9.0 | 8.5 | 8.0 | 8.5 |
| imidazolin-2-yl)-3- | .250 | 8.3 | 8.3 | 7.3 | 9.0 | 7.5 | 8.0 | 8.5 |
| quinolinecarboxylic | .125 | 9.0 | 7.3 | 5.3 | 6.5 | 6.0 | 6.5 | 5.0 |
| acid | .063 | 4.3 | 6.3 | 3.7 | 4.5 | 5.0 | 5.0 | 6.0 |
|  | .032 | 1.0 | 6.0 | 1.0 | 3.0 | 4.5 | 4.0 | 4.0 |

| Compound | RATE | RAG-WEED | VEL-VET-LEAF | S BAR LY LA | CORN FIELD | COTTON | RICE, NATO | SOY-BEAN AD |
| --- | --- | --- | --- | --- | --- | --- | --- | --- |
| 2-(5-Isopropyl-5- | 1.000 | 9.0 | 8.0 | 9.0 | 9.0 | 9.0 | 9.0 | 6.0 |
| methyl-4-oxo-2- | .500 | 8.3 | 6.0 | 9.0 | 9.0 | 9.0 | 9.0 | 4.7 |
| imidazolin-2-yl)-3- | .250 | 8.0 | 4.7 | 9.0 | 9.0 | 9.0 | 9.0 | 3.0 |
| quinolinecarboxylic | .125 | 5.0 | 3.7 | 9.0 | 9.0 | 9.0 | 9.0 | 2.3 |
| acid | .063 | 1.3 | 3.0 | 9.0 | 9.0 | 8.5 | 7.0 | 2.0 |
|  | .032 | 0.5 | 2.0 | 8.5 | 9.0 | 9.0 | 3.0 | 2.0 |

| Rating System | % Difference in Growth from the Check |
| --- | --- |
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

The data are average values obtained from more than on test.

| Plant Species Used | |
| --- | --- |
| Barnyardgrass | (*Eschinochloa crusgalli*) |

EXAMPLE 4

Preemergence herbicidal evaluation of test compounds

The preemergence herbicidal activity of the compound of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From 4 to 5 weeks after treatment, the tests are terminated and each cup is examined and rated according to the rating system set forth above. The herbicidal proficiency of the active ingredient is evident from the test results which are recorded in Table II below. The data are average values obtained from more than one test.

TABLE II

PRE-EMERGENCE TESTS - RATES IN KG/HA

| Compound | RATE | BARN-YARD-GR | GREEN FOX | P NUT SEDGE | WILD OATS | QUACK GRASS | FLD B INDWD | MRNGL RY SP |
| --- | --- | --- | --- | --- | --- | --- | --- | --- |
| 2-(5-Isopropyl-5- | 8.000 | 9.0 | 9.0 | 9.0 | 9.0 | 9.0 | 9.0 | 8.0 |
| methyl-4-oxo-2- | 1.000 | 9.0 | 9.0 | 9.0 | 9.0 | 9.0 | 9.0 | |
| imidazolin-2-yl)-3- | .500 | 8.5 | 9.0 | 9.0 | 9.0 | 9.0 | 9.0 | 8.0 |
| quinolinecarboxylic | .250 | 9.0 | 9.0 | 9.0 | 9.0 | 9.0 | 9.0 | 7.0 |

TABLE II-continued

| | PRE-EMERGENCE TESTS - RATES IN KG/HA | | | | | | | |
|---|---|---|---|---|---|---|---|---|
| acid | .125 | 9.0 | 8.5 | 9.0 | 9.0 | 9.0 | 9.0 | 7.0 |
| | .063 | 6.0 | 7.0 | 7.5 | 8.5 | 8.5 | 9.0 | 3.0 |
| | .032 | 2.0 | 5.0 | 7.5 | 7.5 | 7.0 | 9.0 | 1.0 |

| Compound | RATE | RAG-WEED | VEL-VET-LEAF | S BAR LY LA | CORN FIELD | COTTON | RICE, NATO | SOY-BEAN AD |
|---|---|---|---|---|---|---|---|---|
| 2-(5-Isopropyl-5- | 8.000 | 9.0 | 8.0 | | | | | |
| methyl-4-oxo-2- | 1.000 | 9.0 | 9.0 | 9.0 | 9.0 | 9.0 | | 9.0 |
| imidazolin-2-yl)-3- | .500 | 9.0 | 8.5 | 9.0 | 9.0 | 9.0 | 9.0 | 5.5 |
| quinolinecarboxylic | .250 | 8.5 | 8.0 | 9.0 | 9.0 | 9.0 | 9.0 | 3.0 |
| acid | .125 | 8.0 | 7.5 | 9.0 | 9.0 | 9.0 | 9.0 | 3.0 |
| | .063 | 6.5 | 5.5 | 8.5 | 9.0 | 8.0 | 3.0 | 1.5 |
| | .032 | 3.5 | 4.5 | 8.5 | 9.0 | 7.0 | | 1.0 |

We claim:

1. A process for the preparation of a compound of formula

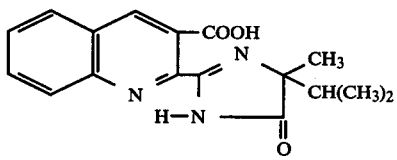

comprising reacting one molar equivalent of a compound of formula

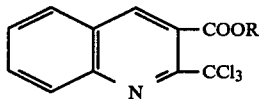

wherein R is $C_1$–$C_3$ alkyl with from one molar equivalent to two molar equivalents of 2-amino-2,3-dimethylbutyramide; in the presence of an inert solvent of benzene, toluene or xylene; and from 3 molar equivalents to 5 molar equivalents of anhydrous sodium or potassium hydroxide; 2 molar equivalents of anhydrous sodium or potassium carbonate, and from 0.1 molar equivalent to 0.3 molar equivalent of a phase transfer catalyst of tetra($C_3$–$C_6$)alkylammonium salts, benzyltri($C_1$–$C_6$)alkylammonium salts, crown ethers or tetraalkylphosphonium salts; from 80° C. to 130° C. or at the atmospheric boiling point of the solvent for a period of time sufficient to essentially complete the reaction.

2. A process according to claim 1, wherein the amount of 2-amino-2,3-dimethylbutyramide is one molar equivalent; the solvent is toluene; the amount of sodium hydroxide is 3.3 molar equivalents; the amount of potassium carbonate is two molar equivalents; the phase transfer catalyst is tetrabutylammonium hydrogen sulfate used in a 0.1 molar equivalent amount; and the temperature of the reaction is the atmospheric boiling point of toluene.

3. A compound of the formula:

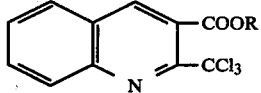

wherein R is $C_1$–$C_3$ alkyl.

4. A compound according to claim 3, ethyl 2-trichloromethyl-3-quinolinecarboxylate.

* * * * *